United States Patent [19]

Di Salvo

[11] 4,355,639

[45] Oct. 26, 1982

[54] APPARATUS FOR THE PARENTERAL ADMINISTRATION OF LIQUIDS AT A CONSTANT, ADJUSTABLE FLOW RATE

[75] Inventor: Francesco Di Salvo, Como, Italy

[73] Assignee: Sis-Ter S.p.A., Palazzo Pignano, Italy

[21] Appl. No.: 166,842

[22] Filed: Jul. 8, 1980

[30] Foreign Application Priority Data

May 21, 1980 [IT] Italy .................. 22227 A/80

[51] Int. Cl.³ .............................................. A61M 5/14
[52] U.S. Cl. ...................... 128/214 R; 128/DIG. 13; 137/510
[58] Field of Search ........... 128/214 R, 214 C, 214 Z, 128/214 E; 137/510

[56] References Cited

U.S. PATENT DOCUMENTS

| | | | |
|---|---|---|---|
| 2,610,645 | 9/1952 | Wagner | 137/510 X |
| 3,298,367 | 1/1967 | Bergman | 128/214 R |
| 3,662,779 | 5/1972 | Weber et al. | 137/510 X |
| 3,776,229 | 12/1973 | McPhee | 128/214 C |
| 3,931,818 | 1/1976 | Goldowsky | 128/214 C |
| 3,965,895 | 6/1976 | Dabney | 128/214 C |
| 4,177,808 | 12/1979 | Malbec | 128/214 R |
| 4,186,740 | 2/1980 | Guerra | 128/214 R |
| 4,203,465 | 5/1980 | Rissi | 137/510 X |
| 4,243,031 | 1/1981 | Genese | 128/214 E |
| 4,252,116 | 2/1981 | Genese et al. | 128/214 G |

FOREIGN PATENT DOCUMENTS 757231 6/1933 France .
7917869 3/1980 France .

*Primary Examiner*—Dalton L. Truluck
*Attorney, Agent, or Firm*—Frishauf, Holtz, Goodman & Woodward

[57] ABSTRACT

To provide for constant and easily adjusted flow rate of liquids from a container (5), which may be a flexible bag, an indexed feeding chamber (1) is directly connected by gravity with the liquid container (5) and provided with a tubular passage (12) therethrough communicating with the outside, preferably through a filter at an end and with the chamber bottom at the other end. The bottom of the feeding chamber (1) is connected to a dripping tube (1A) positioned below, which in turn communicates with the inlet (21) of a device (2) for the microregulation and stabilization of the liquid flow rate. This device, essentially consists of a holder (44) with a cavity (51) therein and two tubular inlet (41) and outlet (47) passages connecting said cavity with the outside, and having a flexible membrane (43) removably covering the opening of the outlet passage within the cavity. Device (2) is height adjustably supported by a slider (31) on a scale (3) fixed to the stand (4) which supports the liquid container (5).

12 Claims, 4 Drawing Figures

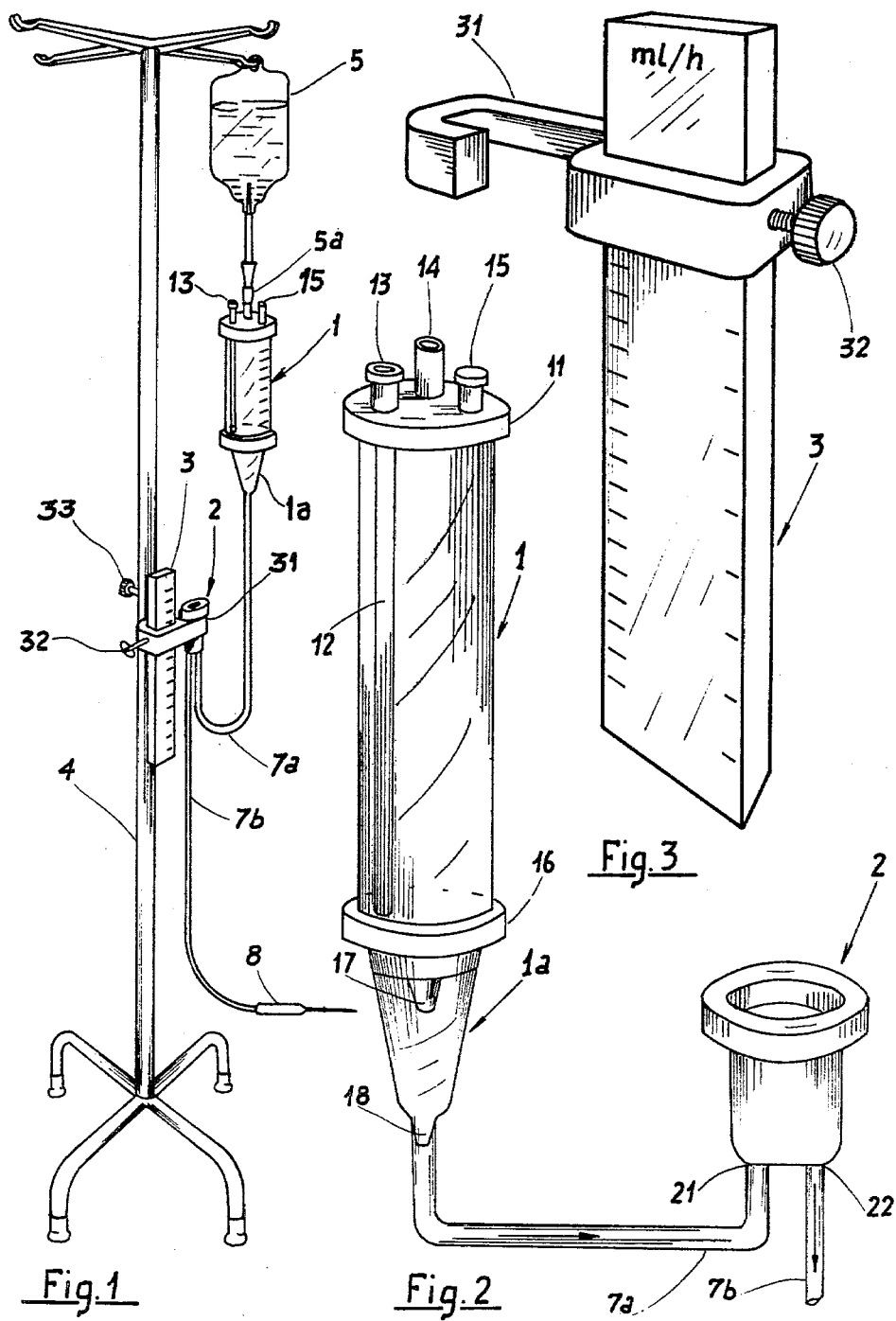

APPARATUS FOR THE PARENTERAL ADMINISTRATION OF LIQUIDS AT A CONSTANT, ADJUSTABLE FLOW RATE

The present invention relates to an apparatus for the parenteral administration of liquids at a constant and adjustable flow rate.

Background: Parenteral administration of liquids to patients is well known in medicine, such as by phleboclysis i.e. perfusion in a patient's vein of a medicated solution, or when the liquid is an anesthetic, or in case of blood transfusion. In any case a flexible tube, usually of a plastic, is connected at one end to a container of the liquid to be administered, being provided at the other end with a cannula or a needle for the insertion into the body, usually a vein, of the patient. The liquid is allowed to flow by gravity from the container hung at an appropriate height. The flow is regulated by means of any device capable of reducing the flow cross-section of the flexible tube by means of a choke or throat of predetermined size. An important requirement is that the administration is performed at an constant and adjustable flow rate.

The devices so far adopted for the above-mentioned purpose, typically represented by MOHR clamps, not only do not ensure that the administration is effected under conditions of constant flow rate, but also do not provide for a fine regulation of such flow rates. Furthermore the compressive action applied by the clamp to the flexible wall of the tube causes an alteration of the physical structural characteristics of the tubular section subject to the action of the clamp, with a progressive loss of elasticity and increasing damages which may result in the cracking and finally breaking of the tube.

These difficulties may prove to be serious especially in those cases where the liquid administration should be carried out at a flow rate value to be selected with utmost care and precision, and where such a value must be kept the same over a substantial period of time. In these cases the flow rate of the liquid is determined through the count of drops and the measurement of the volume occupied by a given number of drops. Thus a certain number of attempts are required involving the administration of improper doses of pharmaceuticals, which may result to be dangerous to the patient, in particular when anesthetics are concerned.

In order to overcome such difficulties, devices employing capillary tubes have been studied and utilized, which give a constant resistance to the flow of the liquid from a container to the end portion of the administration apparatus. Such devices are, however, unsatisfactory in respect of the regulation of the liquid flow rate values, as it is necessary to position the container at different heights with reference to the administration cannula, or to insert in the apparatus one or more devices in series, according to the U.S. Pat. No. 3,878,879, or to utilize one or more capillary tubes in parallel, according to the U.S. Pat. No. 3,298,367.

It is true that for some time certain electronic devices have entered in use, which automatically control the flow rate of the liquid to be administered. However their utilization, due to their cost, is restricted to those cases where is absolutely necessary to have a critical dosage of particularly active medicinal substances or anesthetics, that is when an excessive dose of liquid could give rise to a serious damage to the patient being treated.

It is thereby evident that there is a need for some time to substitute in place of the above-mentioned known devices for the regulation of flow, an apparatus which will not show the previously explained disadvantages and can afford a fine regulation of the flow rate as well as the maintenance thereof at a preselected value during a substantial period of time without the need of the continuous intervention of an operator required to perform troublesome operations, or the adoption of costly electronic apparatuses.

Flexible containers or bags of plastics are more and more used instead of rigid wall vessels such as glass bottles for the parenteral administration of liquids. These flexible containers are preferred because they take up substantially no room during their transportation without liquid therein and because in use, for the outflow of the liquid, no device for the inlet of air in the container is necessary, as the liquid is caused to flow by the external atmospheric pressure acting onto the flexible walls of the container. Therefore, when using certain devices for the regulation of the flow rate, which give a constant flow for a constant difference of pressure between the level of liquid in the container and an operative portion of the device itself, the pressure difference will vary continuously as the liquid level descends.

Under these circumstances the flow rate decreases as the height of the liquid in the container descends and therefore the operation of this type of regulating device is unsatisfactory with containers having flexible walls.

THE INVENTION

It is therefore an object of the present invention to provide an apparatus for the parenteral administration of liquids at a constant, and controllable flow rate, which easily and readily allows a find adjustment and regulation of the liquid to be administered, flowing through a flexible tubular conduit even from a flexible wall container, at the same time rendering it possible to maintain the flow rate at a preselected value for long periods of time, without any need of further interventions or verifications by the operator, and also without causing any wear of the flexible tube or requiring the utilization of complex and expensive electronic apparatus.

Briefly, according to the present invention, a feeding chamber is provided at its upper portion with a covering means having inlet means for the liquid to be connected with the bottom of a container of the liquid, and with tubular means passing through said covering means and communicating at the upper end with the outside; a dripping tube has its upper portion sealed to the bottom of said feeding chamber; a device is provided for the stabilization of the flow rate comprising a holder body with a cavity therein and two tubular inlet and outlet passages connecting said cavity with the outside, and having a flexible membrane removably covering the opening of the outlet passage within the cavity. The inlet passage, of diameter smaller than the outlet is being connected to the bottom of said dripping trough. The outlet passage, is connected through a flexible tube to a cannula for the administration of the liquid.

A stationary scale with a slider thereon height-adjustably supports said stabilization device, there being provided stop means for the fastening of said slider on said scale.

The operation of the stabilization device being part of the present invention is based on the application of a controlled difference of piezometric load to a tubular passage of small, and even capillary cross-section, which provides for a known hydraulic resistance to the liquid flow. Therefore, assuming that the pressure and the piezometric load upstream of the membrane of the device is perfectly known and stable, such as when rigid containers of the liquid are used, e.g., transfusion bottles in which the atmospheric pressure is ensured at the height of the hole for air inlet. A constant flow rate is guaranteed regardless of the quantity of liquid in the bottle.

When the container is of the flexible type, as presently preferred, the flow rate might vary. However, according to a feature of the present invention, the tubular means passing through the feeding chamber until reaching its bottom causes this zone to be connected with the outside at the atmospheric pressure, thus keeping constant the above-defined difference of pressure, and thereby the flow rate as previously stated. With the stabilization device at a predetermined position on the scale, the height difference or piezometric load between the membrane of the device and the air inlet into the feeding chamber is constant, whereby the lowering of the liquid level in the container is of no consequence and the flow rate does not decrease, remaining constant during the whole administration.

DRAWINGS

FIG. 1 is a perspective diagrammatic view of the complete apparatus of the invention;

FIG. 2 is a front view, more in detail, of some components of the apparatus, such as the feeding chamber, the dripping trough and the flow stabilization device;

FIG. 3 shows the scale as an indexed rod with the sliding support of the stabilization device.

DETAILED DESCRIPTION OF THE PREFERRED EMBODIMENT

Figure 4:
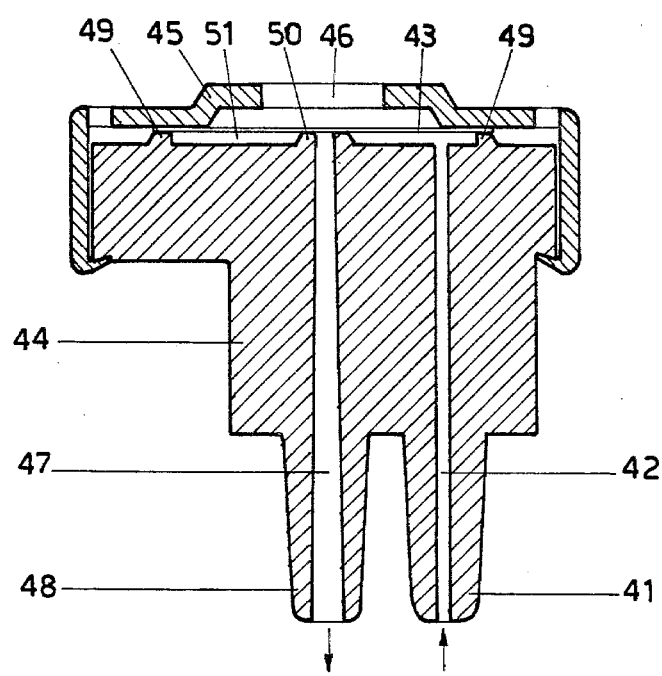
FIG. 4 is a sectional view of a preferred embodiment of the flow stabilization device.

A device 2 (FIG. 1) stabilizes the flow. It will be described in detail below. Device 2 has an inlet tubular passage 21 (FIG. 2) and an outlet tubular passage 22, the latter being connected through a flexible tube 7b to a cannula or needle 8 for the parenteral administration of a liquid. The inlet passage 21 is connected through another section of flexible tube 7a to a unit comprising a feeding chamber 1 and a dripping tube or funnel 1a, which according to the invention renders it possible to use the device 2 also with a container of the liquid to be administered formed as a flexible bag 5, of the most preferred type at present, instead of the conventional rigid vessels such as glass bottles.

The feeding chamber 1 (FIG. 2) preferably of cylindrical shape is provided at its upper portion with a cover 11, formed with a number of passages therethrough, one of which is a tube 12 extending longitudinally along the whole chamber until reaching the chamber bottom. The opposite or upper end of tube 12 is in communication with the outside, preferably through an unknown antibacterial filter 13, as known, to prevent contamination of the liquid to be administered. A second hole 14 through cover 11, to admit the liquid, is connected to a flexible tube 5a from the container 5 which could be a usual bottle of glass or rigid plastic. A third through hole 15 of the cover 11 is, in use, closed by a cap of rubber latex or other elastomeric material.

The feeding chamber 1 is preferably indexed along its length (FIG. 1) to have an indication of the volume of liquid collected therein before passing to the dripping tube 1a below. Dripping tube 1a is sealed to the bottom of chamber 1 by means of a ring nut 16 with gaskets, if required. The liquid descends to the tube 1a from the bottom of the chamber 1 by a passage through a connecting tang or fitting 17 which has a through hole of 0.3–3 mm diameter. The dripping tube 1a is preferably formed of a flexible or elastic material to allow, by pressing thereon, the liquid to flow down from the upper container 5. Dripping tube 1a terminates at the lower end with another fitting 18 for the connection with the tube 7a to the inlet of the stabilization device 2, as already described.

With reference to FIGS. 1, 3, an indexed rod or scale 3 with a slider 31 is fixed height adjustably by clamp 32 to a conventional stand 4. A flexible bag or a rigid bottle hangs from an arm of stand 4. The slider 31 is shaped at one side to provide a seat for holding and supporting the device 2. The slider 31 is height-adjustably secured to the scale rod 3, such as by a screw clamp 32. The scale rod 3, in turn, is adjustably attached to the stand 4 by another clamp 33. By varying the position of the device 2 clamped to the scale rod 3 on the stand 4 with respect to its elevation, the flow rate values are consequently varied. Therefore, certain operations of calibration will be required to readily obtain accurate values of flow rate and will be better described in the following:

With reference to FIG. 4 the device 2 for the stabilization and regulation of the flow rate comprises a holder body 44 with two tubular passages 42, 47 therethrough and a presser element 45, forming a cap thereon. The upper face of body 44 shows an annular projection 49 and a central projection 50 on both of which a membrane 43 is positioned, formed of any suitable flexible material which is chemically inert with respect to the liquid to be administered.

The presser element 45 is firmly secured to the body 44 locking the membrane 43 along a circular zone between the annular projection 49 and the corresponding opposite zones of the presser element 45.

The membrane 43 simply rests on the central projection 50. The presser element or cap 45 has a central opening 46 which therefore places the central cavity defined between the body 44 and the presser 45 in pneumatic pressure communication with the outside environment, so that in this case the reference pressure is equal to the atmospheric pressure. The lower face of the membrane 43 and the part of the upper face of body 44 between the annular projection 49 and the central projection 50 define an annular chamber 51 or cavity into which leads the upper end of the passage 42. Passage 42 is of smaller diameter than the passage 47 and may be of capillary size. The upper end of the tubular passage 47 leads into the central zone of the projection 50, in contact with the membrane. The opposite ends of the narrower passage 42 and of the tubular passage 47 lead respectively into conectors 41 and 48, corresponding to said inlet and outlet passages 21, 22, as schematically shown by the arrows in FIG. 4, and the tubular conduits 7a, 7b.

Operation: The liquid arrives in the device from the dripping tube a through connector 41 and passage 42, thus coming into contact with membrane 43. Membrane 43 tends to flex upwardly, pushing the air located above it to the outside through opening 46 of presser element 45. The liquid can thus enter into outlet passage 47 and, through connector 48, pass to the discharge line 7b connected to the patient.

The flow rate is determined by the reference pressure, in this case the atmospheric pressure, by the height difference between the membrane, and the level of liquid in the dripping tube 1a. The pressure in tube 1a is also atmospheric pressure due to the tubular passage 12. The difference in level between tube 1a and device 2, and the known hydraulic resistance of the narrow, or capillary passage 41, determines the flow rate of the liquid without any effect of pressure of the liquid in the container 5 which may be variable, when this is a flexible bag. The regulation of the flow rate may then simply be effected through variations in height of the pressure control device 2 by properly positioning the slider 31 supporting the device 1 on the scale rod 3.

The arrangement has the advantage to obtain an exactly constant flow rate for long periods of time, merely upon an initial calibration without the need of test administrations or attempts at flow rates and dosages different from those prescribed, which could be noxious to the patient. An initial calibration is necessary whenever the scale rod 3 is repositioned along the upright stand 4. It is carried out by simply positioning the membrane 43 of the device 2 at a reference index on the scale 3 and moving scale rod 3 along support 4 until the device 2 is even with the level of liquid in tube 1a. The flow rate is then adjusted during the administration of the liquid even by a non-specialized operator by properly changing the position of the slider 31 with the device 1 thereon along the scale 3. Readjustment by changing the position of slider 31 is simple.

Various additions and/or modifications can be made within the scope of the invention.

What I claim is:

1. Apparatus for the parenteral administration of a liquid at a constant, adjustable flow rate, comprising
    means (5, 1) supplying said liquid under essentially constant, controlled conditions of pressure and having a supply outlet (17);
    a dripping tube or funnel (1a) secured to said liquid supply means;
    support means (4) supporting said dripping tube or funnel (1a) at a predetermined level or elevation;
    a flow stabilization device (2) including
    a body (44) formed with
    a cavity (51) therein,
    a tubular inlet passage (42) communicating with said cavity and a first tubing (7a) connecting said inlet passage with the bottom of said dripping tube or funnel (1a),
    a tubular outlet passage (47) communicating with said cavity, and a second tubing (7b) adapted for connection of said outlet passage to a cannula (8) for administration of the liquid to a patient,
    said inlet passage (42) having a smaller diameter than the outlet passage (47),
    and a flexible membrane (43) closing off said cavity against ambient air and further removably covering the opening of the outlet passage (47) within the cavity;
    a stationary scale (3) vertically positioned at a controlled level with respect to said predetermined level or elevation;
    a slider (31) slidable vertically along said stationary scale for vertical adjustment therealong positioned at an elevation below said predetermined level or elevation supported by said slider and vertically adjustably positioned thereby;
    and means (32) for securing said slider (31) and hence said stabilization device (2) in vertically adjustable position along said scale to permit reproducibly adjustably positioning of said stabilization device at a level below said predetermined level and to permit controlled flow from said dripping tube or funnel (1a) to and through said stabilization device (2) as a function of level difference between the liquid level in said dripping tube or funnel (1a) and said stabilization device.

2. Apparatus according to claim 1, wherein said liquid supply means includes a vertically positioned elongated feeding chamber, a first feed-through tube (12) extending through said feeding chamber essentially to the bottom thereof, and connected to a supply container (5) of the liquid to be administered.

3. An apparatus according to claim 2, wherein said feeding chamber (1) is cylindrical and indexed along its length, with a scale indicating the volume of liquid contained therein.

4. An apparatus according to claim 1, wherein said dripping tube or funnel (1a) is formed with flexible walls.

5. Apparatus according to claim 2, wherein the bottom of said feeding chamber (1) has an outlet to said dripping tube or funnel (1a) of a diameter between 0.3 and 3 mm.

6. An apparatus according to claim 1, wherein said slider is formed on one side to form a seat (31) for holding and supporting said stabilization device (2) and wherein said stop means comprises a screw clamp (32).

7. Apparatus according to claim 1, wherein said means supporting said dripping tube or funnel (1a) comprises an upright stand (4);
    and said scale (3) is height-adjustably secured to said stand.

8. An apparatus according to claim 1 wherein the body (44) of said stabilization device (2) has an upper face formed with a recess and an annular outer projection (49) surrounding the recess, the cavity (51) being defined by the recess inwardly of said projection;
    a central projection (50) extending from the recess;
    and means (45) for clamping said membrane (43) along said annular projection while leaving it free to rest on or lift off said central projection.

9. An apparatus according to claim 8, wherein said outlet passage (47) communicates with said cavity (51) through a hole in the central zone of said central projection (50).

10. Apparatus according to claim 2, including an anti-bacterial filter (13) providing air communication between said feed-through tube (12) extending into said feeding chamber (1) and the interior of said chamber.

11. An apparatus according to claim 1, wherein said inlet passage (42) of said stabilization device (2) is of a capillary size.

12. Apparatus according to claim 8, wherein said clamping means for the membrane (43) comprises a presser element (45) secured on the holder body and engaging the membrane.

* * * * *

UNITED STATES PATENT AND TRADEMARK OFFICE
CERTIFICATE OF CORRECTION

PATENT NO. : 4,355,639

DATED : October 26, 1982

INVENTOR(S) : Francesco DI SALVO

It is certified that error appears in the above—identified patent and that said Letters Patent is hereby corrected as shown below:

On the title page insert in the heading the following:
--This application is a Continuation-in-Part of my earlier application, Serial No. 973,891, filed December 28, 1978, entitled "APPARATUS FOR THE MICROREGULATION OF FLOW AND STABILIZATION OF FLOW RATE, PARTICULARLY FOR PERFUSION AND TRANSFUSION APPARATUS", now abandoned.--.

In the title heading, item 30, "Foreign Application Priority Data", add:

--January 12, 1978 [IT] Italy 19206A/78--.

Signed and Sealed this

Eighteenth Day of January 1983

[SEAL]

Attest:

GERALD J. MOSSINGHOFF

Attesting Officer

Commissioner of Patents and Trademarks